United States Patent
Liu et al.

(10) Patent No.: US 7,385,088 B1
(45) Date of Patent: Jun. 10, 2008

(54) **COMPOUNDS FROM *ANTRODIA CAMPHORATA***

(75) Inventors: Sheng-Yun Liu, Taipei Hsien (TW);
Mao-Tien Kuo, Taipei Hsien (TW);
Wu-Che Wen, Taipei Hsien (TW)

(73) Assignee: Golden Biotechnology Corporation, Taipei Hsien (TW)

( * ) Notice: Subject to any disclaimer, the term of this patent is extended or adjusted under 35 U.S.C. 154(b) by 0 days.

(21) Appl. No.: 12/021,584

(22) Filed: Jan. 29, 2008

(30) Foreign Application Priority Data

Oct. 19, 2007 (TW) .............................. 96139241 A

(51) Int. Cl.
*C07C 49/543* (2006.01)
*A61K 31/12* (2006.01)

(52) U.S. Cl. ...................................... 568/377; 514/690

(58) Field of Classification Search .................. 568/377; 514/690
See application file for complete search history.

(56) References Cited

OTHER PUBLICATIONS

"New Steroid Acids from *Antrodia cinnamomea*, A fungal Parasite of *Cinnamomum micranthum*", Chung-Hsiung Chen et al., *Journal of Natural Products*, vol. 58, No. 11, p. 1655, Nov. 1995.
"Three new Triterpenoids from *Antrodia cinnamomea*", I-Hwa Cherng et al., *Journal of Natural Products*, vol. 58, No. 3, p. 365, Mar. 1995.
"Triterpenoids from *Antrodia cinnamomea*", I-Hwa Cherng et al., *Phytochemistry*, vol. 41, No. I, pp. 263-267, 1996.
"A Sesquiterpene Lactone, Phenyl and Biphenyl compounds from *Antrodia cinnamomea*", Hung-Chen Chiang et al., *Phytochemistry*, vol. 39, No. 3, pp. 613-616, 1995.
"Steroids and Triterpenoids of *Antodia cinnamomea*-A fungus Parasitic on *Cinnamomum micranthum*", Shu-Wei Yang et al., *Phytochemistry*. vol. 41, No. 5, pp. 1389-1392, 1996.

*Primary Examiner*—Sikarl A Witherspoon
(74) *Attorney, Agent, or Firm*—Rabin & Berdo, P.C.

(57) ABSTRACT

The present invention relates to a novel compound and use thereof, in particular to Antroquinonol B and Antroquinonol C isolated from *Antrodia camphorata* extracts which can effectively inhibit the growth of cancer cells. The compounds from *Antrodia camphorata* are first reported, which can be applied not only in inhibiting growth of breast cancer, lung cancer, hepatic cancer and prostate cancer, but also in anti-cancer medicinal compositions for the abovementioned cancer cells.

16 Claims, No Drawings

COMPOUNDS FROM *ANTRODIA CAMPHORATA*

BACKGROUND OF THE INVENTION

1. Field of the Invention

The present invention relates to novel compounds and use thereof, in particular to Antroquinonol B and Antroquinonol C compounds isolated from *Antrodia camphorata* extracts and their use in growth inhibition of tumor cells. The compounds from *Antrodia camphorata* are first reported, which can be applied not only in inhibiting growth of breast cancer, lung cancer, hepatic cancer and prostate cancer, but also in anti-cancer medicinal compositions for the above-mentioned cancer cells.

2. The Prior Arts

*Antrodia camphorata* is also called Chang-Zhi, Niu Chang-Gu, red camphor mushroom and the like, which is a perennial mushroom belonging to the order Aphyllophorales, the family Polyporaceae. It is an endemic species in Taiwan growing on the inner rotten heart wood wall of *Cinnamomum kanehirae* Hay. *Cinnamoum kanehirai* Hay is rarely distributed and being overcut unlawfully, which makes *Antrodia camphorata* growing inside the tree in the wild became even rare. The price of *Antrodia camphorata* is very expensive due to the extremely slow growth rate of natural *Antrodia camphorata* that only grows between Junes to October.

The fruiting bodies of *Antrodia camphorata* are perennial, sessile, hard and woody, which exhales strong smell of sassafras (camphor aroma). The appearances are various with plate-like, bell-like, hoof-like, or tower-like shapes. They are reddish in color and flat when young, attached to the surface of wood. Then the brims of the front end become little curled tilted and extend to the surroundings. The color turns to be faded red-brown or cream yellow brown, with ostioles all over. This region is of very high medical value.

In traditional Taiwanese medicine, *Antrodia camphorata* is commonly used as an antidotal, liver protective, anti-cancer drug. *Antrodia camphorata*, like general edible and medicinal mushrooms, is rich in numerous nutrients including triterpenoids, polysaccharides (such as β-glucosan), adenosine, vitamins (such as vitamin B, nicotinic acid), proteins (immunoglobulins), superoxide dismutase (SOD), trace elements (such as calcium, phosphorus and germanium and so on), nucleic acid, steroids, and stabilizers for blood pressure (such as antodia acid) and the like. These physiologically active ingredients are believed to exhibit effects such as: anti-tumor activities, increasing immuno-modulating activities, anti-allergy, anti-bacteria, anti-high blood pressure, decreasing blood sugar, decreasing cholesterol, and the like.

Triterpenoids are the most studied component among the numerous compositions of *Antrodia camphorata*. Triterpenoids are the summary terms for natural compounds, which contain 30 carbon atoms with the pent acyclic or hex acyclic structures. The bitter taste of *Antrodia camphorata* is from the component of triterpenoids. Three novel ergostane-type triterpenoids (antcin A, antcin B, antcin C) Were isolated by Cherng et al. from the fruiting bodies of *Antrodia camphorata* (Cherng, I. H., and Chiang, H. C. 1995. Three new triterpenoids from *Antrodia cinnamomea*. J. Nat. Prod. 58:365-371). Three new compounds zhankuic acid A, zhankuic acid B and zhankuic acid were extracted from the fruiting bodies of *Antrodia camphorata* with ethanol by Chen et al. (Chen, C. H., and Yang, S. W. 1995. New steroid acids from *Antrodia cinnamomea*,—a fungus parasitic on *Cinnamomum micranthum*. J. Nat. Prod. 58:1655-1661). In addition, Cherng et al. also found three other new triterpenoids from the fruiting bodies of *Antrodia camphorata*, which are sesquiterpene lactone and 2 biphenyl derived compounds, 4,7-dimethoxy-5-methyl-1,3-benzodioxole and 2,2',5,5'-teramethoxy-3,4,3',4'-bi-methylenedioxy-6,6'-dimethylbiphenyl (Chiang, H. C., Wu, D. P., Cherng, I. W., and Ueng, C. H. 1995. A sesquiterpene lactone, phenyl and biphenyl compounds from *Antrodia cinnamomea*. Phytochemistry. 39:613-616). In 1996, four novel ergostane-type triterpenoids (antcins E and F and methyl antcinates G and H) were isolated by Cherng et al. with the same analytic methods (Cherng, I. H., Wu, D. P., and Chiang, H. C. 1996. Triteroenoids from *Antrodia cinnamomea*. Phytochemistry. 41:263-267). And two ergostane related steroids, zhankuic acids D and E together with three lanosta related triterpenes, 15 alpha-acetyl-dehydrosulphurenic acid, dehydroeburicoic acid, dehydrosulphurenic acid were isolated by Yang et al. (Yang, S. W., Shen, Y. C., and Chen, C. H. 1996. Steroids and triterpenoids of *Antrodia cinnamomea*—a fungus parasitic on *Cinnamomum micranthum*. Phytochemistry. 41:1389-1392).

Although *Antrodia camphorata* extracts were reported to have the anti-tumor effects from previous experiments (such as the reference mentioned above: Chen & Yang, 1995), further experiments are needed to identify the effective composition for tumor inhibition. The application in cancer therapy will be of great beneficial effects if the real effective compositions are found.

SUMMARY OF THE INVENTION

In order to identify the compounds containing anti-tumor effects from the extracts of *Antrodia camphorata*, the compound of formula (1) was isolated and purified in the present invention, where X can be hydroxyl (—OH) or methoxy (—OCH$_3$).

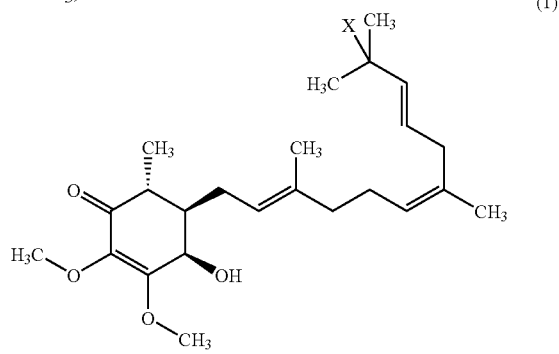

(1)

When X is hydroxyl, the structure is as shown in formula (2). The chemical name is Antroquinonol B, with molecular formula of $C_{24}H_{38}O_5$ and molecular weight of 406.

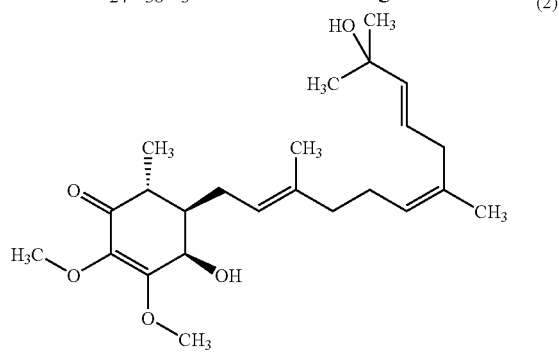

(2)

When X is methoxy, the structure is as shown in formula (3). The chemical name is Antroquinonol C, with molecular formula of $C_{25}H_{40}O_5$ and molecular weight of 420.

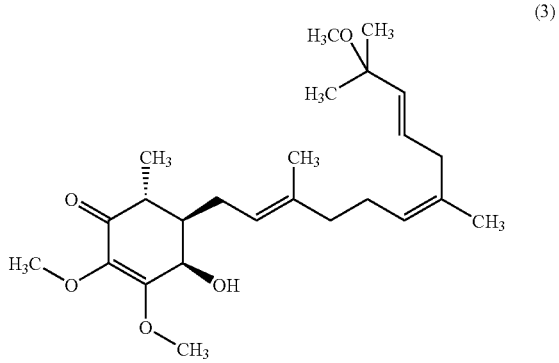

(3)

Compounds Antroquinonol B and Antroquinonol C are purified from aqueous extraction or organic solvent extraction of *Antrodia camphorata*. The organic solvents used include, but not limited to, alcohols such as methanol, ethanol or propanol, esters such as ethyl acetate, alkanes such as hexane, or halogenated alkanes such as chloromethane, chloroethane. Among them, alcohol is preferred, and ethanol is particularly preferred.

The abovementioned compounds in the present invention can be applied in inhibiting tumor cell growth, which can further be used as a medicinal composition to treat cancer and to enhance the therapeutic effects. The compounds of the present invention can be applied in inhibiting a range of cancer cells, including breast cancer, lung cancer, hepatic cancer and prostate cancer, leading to a marked slowering of the growth of cancer cells, and further inhibiting proliferation of cancer cells and decreasing the risk of malignancy. Therefore they can be used for the treatment of breast cancer, lung cancer, hepatic cancer, prostate cancer and more.

On the other hand, the compounds of formula (2) and/or formula (3) in the present invention can be incorporated into medicinal compositions for treating breast cancer, lung cancer, hepatic cancer, and prostate cancer to inhibit the growth of tumor cells. The medicinal compositions include not only the effective amounts of Antroquinonol B and Antroquinonol C, but also the pharmaceutically accepted carries. The carriers include, but are not limited to, excipients such as water, fillers such as sucrose or starch, binders such as cellulose derivatives, diluents, disintegrants, absorption enhancers or sweeteners. The compositions of the present invention can be manufactured through mixing the compounds of Antroquinonol B and Antroquinonol C with at least one of the carriers by means of conventional methods known in the pharmaceutically technical field, which can be formulated, but are not limited to, as a powder, tablet, capsule, pellets, granules or other liquid formulation.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

The mycelia, fruiting bodies or mixture of both from *Antrodia camphorata* are first extracted with water or organic solvents to obtain the aqueous extract or organic solvent extract of *Antrodia camphorata* using the methods well known in the arts. The organic solvents include, but not limited to, alcohols such as methanol; ethanol or propanol; esters such as Ethyl acetate; alkanes such as hexane; or halogenated alkanes such as chloromethane, and chloroethane. Among them, alcohol is preferred, and ethanol is particularly preferred.

The aqueous or organic solvent extracts of *Antrodia camphorate* were subjected to high-performance liquid chromatography (HPLC) for isolation and purification. Each fraction was recovered and applied to anti-tumor assay. The potent fractions with anti-tumor ability were analyzed for the composition and further assayed against different cancer cells. The above approach then led to the identification of compounds of Antroquinonol B and Antroquinonol C in inhibiting the growth of breast cancer, lung cancer, hepatic cancer, prostate cancer and more. These compounds from *Antrodia camphorata* are regarded as novel compounds since they have never been reported in any literatures.

The compounds of Antroquinonol B and Antroquinonol C were demonstrated with anti-cancer effects using 3-(4,5-dimethylthiazol-2-yl)-2, S-diphenyl tetrazolium bromide (MTT) assay according to the anti-tumor drugs screening model of National Cancer Institute (NCI) on cell survival rates using cell lines of breast cancer, lung cancer, hepatic cancer, prostate cancer. The above assays had proved that Antroquinonol B and Antroquinonol C decreased survival rates of breast cancer cell lines (MCF-7 and MDA-MB-231), lung cancer cell lines (A-549), hepatocellular carcinoma cell lines (Hep 3B and Hep G2) and prostate cancer cell lines (LNCaP and DU-145), at the same time showed relatively low half-maximal inhibitory concentration ($IC_{50}$) values. Therefore Antroquinonol B and Antroquinonol C can be used in inhibiting cancer cell growth of breast cancer, lung cancer, hepatic cancer, and prostate cancer, which can further be applied in cancer treatment of breast cancer, lung cancer, hepatic cancer, prostate cancer and the like. The details of the examples are described as follows:

Example 1

Isolation of Antroquinonol B and Antroquinonol C

One hundred grams of mycelia, fruiting bodies or mixture of both from *Antrodia camphorata* were placed into a flask. A proper amount of water and alcohol (70-100% alcohol solution) was added into the flask and were stirred at 20-25° C. for at least 1 hour. The solution was filtered through a filter and a 0.45 μm membrane and the filtrate was collected as the extract.

The filtrate of *Antrodia camphorata* was subjected to High Performance Liquid chromatography (HPLC) analysis. The separation was performed on a RP18 column, the mobile phase consisted of methanol (A) and 0.1-0.5% acetic acid (B), with the gradient conditions of 0-10 min in 95%~20% B, 10-20 min in 20%~10% B, 20-35 min in 10%~90% B, 35-40 min in 10%~95% B, at the flow rate of 1 ml/min. The column effluent was monitored with a UV-visible detector.

The fractions collected at 21.2-21.4 min were collected and concentrated to yield Antroquinonol B, a product of pale yellow powder. The analysis of this product showed the molecular formula of $C_{24}H_{38}O_5$, molecular weight of 406. Investigation of NMR spectra showed that $^1$H-NMR (CDCl$_3$) δ (ppm)=1.21, 1.36, 1.67, 1.71, 1.75, 1.94, 2.03, 2.07, 2.22, 2.25, 3.68, 4.05, 5.71, and 5.56; $^{13}$C-NMR (CDCl$_3$) δ (ppm)=12.31, 16.1, 16.12, 17.67, 25.67, 26.44, 26.74, 27.00, 39.71, 39.81, 4.027, 43.34, 59.22, 60.59, 71.8, 120.97, 123.84, 124.30, 131.32, 134.61, 135.92, 138.05, 160.45, and 197.11.

The fractions collected at 23.7-24 min were collected and concentrated to yield Antroquinonol C, a product of pale yellow powder. The analysis of this product showed the molecular formula of $C_{25}H_{40}O_5$, molecular weight of 420. Investigation of NMR spectra showed that $^1$H-NMR (CDCl$_3$) δ (ppm)=1.21, 1.36, 1.67, 1.71, 1.75, 1.94, 2.03, 2.07, 2.22, 2.25, 3.24, 3.68, 4.05, 5.12, 5.50, and 5.61; $^{13}$C-NMR (CDCl$_3$) δ (ppm)=12.31, 16.1, 16.12, 17.67, 24.44, 26.44, 26.74, 27.00, 37.81, 39.81, 4.027, 43.34, 49.00, 59.22, 60.59, 120.97, 123.84, 124.30, 135.92, 138.05, 160.45, and 197.12.

The structures of Antroquinonol B and Antroquinonol C were compared in the chemical compound database. No compound with similar structure was discovered. Therefore, these compounds are regarded as novel compounds since they have never been reported previously.

Example 2

Ex Vivo Survival Assay for Anti-Breast Cancer Effects

The NCI anti-cancer drug screen model was adopted to test the anti-cancer effect of the isolated compounds from example 1 in the present invention. The isolated Antroquinonol B and Antroquinonol C from example 1 were added into the culture media of human breast-cancer cells, MCF-7 or MDA-MB-231, to test for tumor cell survival. This survival assay was carried out with the widely known MTT (3-[4,5-dimethylthiazol-2-yl]2,5-diphenyltetrazolium bromide) assay. MCF-7 cell line is originated from primary breast cancer cells (early stage), sensitive to estrogen and therefore is estrogen-dependent, while MDA-MB-231 is insensitive to estrogen and therefore is estrogen-independent, which is a difficult tumor with a low survival rate.

MTT assay is commonly used to determine cell proliferation, percent of viable cells, and cytotoxicity. 3-[4,5-dimethylthiazol-2-yl]2,5-diphenyltetrazolium bromide (MTT) is a yellow dye, which can be absorbed by the living cells and be reduced to purplish blue formazan crystals by succinate tetrazolium reductase in mitochondria. Formazan formation can therefore be used to assess and determine the survival rate of cells.

The human breast-cancer cells, MCF-7 (purchased from the Bioresources Collection and Research Center (BCRC) with the accession number of BCRC60436) and MDA-MB-231 (purchased from National Health Research Institutes (NHRI) with the accession number of CCRC 60425) were cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate. Total ethanol extracts of Antrodia camphorata without purification (the control group), Antroquinonol B or Antroquinonol C (the experimental group) were added into each of the 96 wells at the following concentrations: 30, 10, 3, 1, 0.3, 0.1 and 0.03 µg/ml, respectively. The cells were incubated at 37° C. in a 5% CO$_2$ incubator for 48 hours. MTT was added in a concentration of 2.5 mg/ml into each well in dark and incubated for 4 hours, followed by the addition of 100 µl of lysis buffer to stop the reaction. The plates were read on an ELISA reader at wavelength of 570 nm to determine the survival rates. The half maximal inhibitory concentration (IC$_{50}$) values were also calculated and listed in Table 1.

TABLE 1

Results of ex vivo survival assay for inhibition of breast cancer cells

| | | IC$_{50}$ (µg/ml) | |
|---|---|---|---|
| | Samples | MCF-7 | MDA-MB-231 |
| Control group | Crude extracts of A. camphorata | 11.13 | 25.81 |
| Experiment group | Antroquinonol B | 1.94 | 8.72 |
| | Antroquinonol C | 1.17 | 21.9 |

Antroquinonol B and Antroquinonol C are capable of decreasing the survival rate of estrogen-dependent breast cancer cell MCF-7 from the result of Table 1. The IC$_{50}$ value of Antroquinonol B toward MCF-7 was dropped to 1.94 µg/ml, which was 82.56% lower than that of crude extracts from A. camphorata (11.13 µg/ml). And the IC$_{50}$ value of Antroquinonol C toward MCF-7 was dropped to 1.17 µg/ml, which was 89.49% lower than that of crude extracts from A. camphorata (11.13 µg/ml). Therefore Antroquinonol B and Antroquinonol C from Antrodia camphorata can be applied to inhibit the growth of estrogen-dependent breast cancer cells MCF-7.

On the other hand, Antroquinonol B and Antroquinonol C are capable of decreasing the survival rate of estrogen-independent breast cancer cell MDA-MB-231. The IC$_{50}$ values of Antroquinonol B and Antroquinonol C toward MDA-MB-231 were 8.72 µg/ml and 21.9 µg/ml respectively, which were 66.21% and 15.15% lower than that of crude extracts from A. camphorata (25.81 µg/ml). The concentration of Antroquinonol B and Antroquinonol C needed for the half maximal inhibitory concentration of MDA-MB-231 were all lowered than the crude extracts in the control group, and a better inhibitory effect was found in Antroquinonol B. Therefore Antroquinonol B and Antroquinonol C from Antrodia camphorata can be applied to inhibit the growth of estrogen-independent breast cancer cells MDA-MB-231.

Example 3

Ex Vivo Survival Assay for Anti-Lung Cancer Effects

The NCI anti-cancer drug screen model was also employed to test the anti-lung cancer effect of the Antroquinonol B and Antroquinonol C in the present invention. The Antroquinonols isolated from example 1 were added into the culture media of human lung cancer cell A549 with the abovementioned MTT assay to analyze lung cancer cell survival rates.

Human lung cancer cell A549 was obtained from the Bioresources Collection and Research Center (BCRC) of the Food Industry Research and Development Institute with an accession number of BCRC 60074. A549 cells were cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate. Total ethanol extracts of *Antrodia camphorata* without purification (the control group), Antroquinonol B or Antroquinonol C (the experimental group) were added into each of the 96 wells at the following concentrations: 30, 10, 3, 1, 0.3, 0.1 and 0.03 µg/ml, respectively. The cells were incubated at 37° C. in a 5% $CO_2$ incubator for 48 hours. MTT was added in a concentration of 2.5 mg/ml into each well in dark and incubated for 4 hours, followed by the addition of 100 µl of lysis buffer to stop the reaction. The plates were read on an ELISA reader at wavelength of 570 nm to determine the survival rates. The half-maximal inhibitory concentration ($IC_{50}$ values) were also calculated and listed in Table 2.

TABLE 2

Results of ex vivo survival assay for inhibition of lung cancer cells

| | Samples | $IC_{50}$ (µg/ml) A549 |
|---|---|---|
| Control group | Crude extracts of *A. camphorata* | 13.21 |
| Experimental group | Antroquinonol B | 11.9 |
| | Antroquinonol C | 8.21 |

From the result of table 2, Antroquinonol B and Antroquinonol C can effectively decrease the survival rates of human lung cancer cell line A549. The $IC_{50}$ value of Antroquinonol B and Antroquinonol C toward A549 were 11.9 µg/ml and 8.21 µg/ml respectively, which were 9.92% and 37.85% lower than that of crude extracts from *A. camphorata* (13.21 µg/ml). Both Antroquinonol B and Antroquinonol C had reduced $IC_{50}$ values than the control group, and a better inhibitory effect was found in Antroquinonol B. Therefore Antroquinonol B and Antroquinonol C from *A. camphorata* can be applied to inhibit the growth of lung cancer cells A549.

Example 4

Ex Vivo Survival Assay for Anti-Hepatic Cancer Effects

The NCI anti-cancer drug screen model was employed to test the anti-cancer effect of the Antroquinonol B and Antroquinono C in the present invention. The Antroquinonos isolated from example 1 were added into the culture media of human hepatic-cancer cells, Hep 3B or Hep G2, for tumor cell survival assay. Hepatic-cancer cells Hep 3B (BCRC 60434) and Hep G2 (BCRC 60025), were obtained from the Bioresources Collection and Research Center (BCRC) of the Food Industry Research and Development Institute.

The human hepatic-cancer cells, Hep 3B and Hep G2, were cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate. Total ethanol extracts of *Antrodia camphorata* without purification (the control group), Antroquinonol B or Antroquinonol C (the experimental group) were added into each of the 96 wells at the following concentrations: 30, 10, 3, 1, 0.3, 0.1 and 0.03 µg/ml, respectively. The cells were incubated at 37° C. in a 5% $CO_2$ incubator for 48 hours. MTT was added in a concentration of 2.5 mg/ml into each well in dark and incubated for 4 hours, followed by the addition of 100 µl of lysis buffer to stop the reaction. The plates were read on an ELISA reader at wavelength of 570 nm to determine the survival rates. The half-maximal inhibitory concentration ($IC_{50}$) values were also calculated and listed in Table 3.

TABLE 3

Results of ex vivo survival assay for inhibition of hepatic cancer cells

| | | $IC_{50}$ (µg/ml) | |
|---|---|---|---|
| | Samples | Hep3B | HepG2 |
| Control group | Crude extracts of *A. camphorata* | 5.10 | 18.63 |
| Experimental group | Antroquinonol B | 1.21 | 3.32 |
| | Antroquinonol C | 1.32 | 5.12 |

From the result of table 3, Antroquinonol B and Antroquinonol C can effectively decrease the survival rates of human hepatic cancer cell line Hep 3B and Hep G2. The $IC_{50}$ value of Antroquinonol B toward Hep 3B were 1.21 µg/ml, which was 76.27% lower than that of crude extracts from *A. camphorata* (5.10 g/ml). The $IC_{50}$ value of Antroquinonol C toward Hep 3B were 1.32 µg/ml, which was 74.12% lower than that of crude extracts from *A. camphorata*. Both compounds showed remarkedly decrease $IC_{50}$ values than the control group in Hep3B cells. The $IC_{50}$ values of Antroquinonol B and Antroquinonol C toward Hep G2 were 3.32 µg/ml and 5.12 µg/ml respectively, which were 82.18% and 72.52% lower than that of crude extracts from *A. camphorata* (18.63 µg/ml). Both compounds showed remarkedly decrease $IC_{50}$ values than the control group in HepG2 cells. Therefore Antroquinonol B and Antroquinonol C from *A. camphorata* can be applied to inhibit the growth of hepatic cancer cells.

In addition, hepatic cancer cells treated with Antroquinonol B showed lower $IC_{50}$ values than cells treated with Antroquinonol C, that is, lower concentration of Antroquinonol B was needed in inhibiting growth the hepatic cancer cells Hep 3B and Hep G2. Antroquinonol B has better inhibiting effects than Antroquinonol C toward the growth of hepatic cancer cells.

Example 5

Ex Vivo Survival Assay for Anti-Prostate Cancer Effects

The NCI anti-cancer drug screen model was also employed to test the anti-cancer effect of the Antroquinonols in the present invention. Antroquinonol B and Antroquinonol C isolated from example 2 were added into the culture media of human prostate cancer cells, LNCaP or DU-145, and prostate cancer cell survival rates were analyzed with the abovementioned MTT assay. LNCaP is originated from epithelial cells of prostate gland, which depends on androgen in the early stage and thus is androgen-dependent cancer cell. DU-145 is recurrent type prostate cancer cell, which does not rely on androgen for growth and therefore is androgen-independent. This recurrent type prostate cancer has no effective treatment so far. Both LNCaP and DU-145 were ordered from NHRI with accession numbers of CCRC 60088 and CCRC 60348 respectively.

The human prostate-cancer cells, LNCaP and DU-145, were cultivated in media containing fetal calf serum for 24 hours. The proliferated cells were washed once with PBS, then treated with 1× trypsin-EDTA and centrifuged at 1200 rpm for 5 minutes. The supernatant was discarded and the cell pellet was resuspended in 10 ml of fresh culture medium by gently shaking. The cells were placed in a 96-well plate. Total ethanol extracts of *Antrodia camphorata* without purification (the control group), Antroquinonol B or Antroquinonol C (the experimental group) were added into each of the 96 wells at the following concentrations: 30, 10, 3, 1, 0.3, 0.1 and 0.03 μg/ml, respectively. The cells were incubated at 37° C. in a 5% $CO_2$ incubator for 48 hours. MTT was added in a concentration of 2.5 mg/ml into each well in dark and incubated for 4 hours, followed by the addition of 100 μl of lysis buffer to stop the reaction. The plates were read on an ELISA reader at wavelength of 570 nm to determine the survival rates. The half-maximal inhibitory concentration ($IC_{50}$) values were also calculated and listed in Table 4.

TABLE 4

Results of ex vivo survival assay for inhibition of prostate cancer cells

| | | $IC_{50}$ (μg/ml) | |
| --- | --- | --- | --- |
| | Samples | LNCaP | DU-145 |
| Control group | Crude extracts of *A. camphorata* | 11.49 | 41.39 |
| Experimental group | Antroquinonol A | 5.67 | 10.12 |
| | Antroquinonol J | 8.72 | 12.21 |

From the result of table 4, the cell survival rates of LNCaP and DU-145 were effectively reduced through the activities of Antroquinonol B or Antroquinonol C. The $IC_{50}$ values of Antroquinonol B and Antroquinonol C toward LNCaP were 5.67 μg/ml and 8.72 μg/ml respectively, which were 50.65% and 24.11% lower than the $IC_{50}$ value of the control group (11.49 μg/ml). The $IC_{50}$ values of Antroquinonol B and Antroquinonol C toward DU-145 were 10.12 μg/ml and 12.21 μg/ml respectively, which were 75.55% and 70.5% lower than the $IC_{50}$ value of the control group (41.39 μg/ml). Therefore the half maximal inhibitory concentrations of these two Antroquinonols from *A. camphorata* were remarkedly reduced toward prostate cancer cells LNCaP and DU-145 in comparison to the crude extracts in the control group. In addition, LNCaP prostate cancer cells treated with Antroquinonol B showed a much lower $IC_{50}$ values than Antroquinonol C treated cells, that is, a better inhibitory effect was found in Antroquinonol B for inhibiting prostate cancer cells.

On the other hand, both Antroquinonol B and Antroquinonol C can effectively inhibit the growth of LNCaP and DU-145 prostate cancer cells with two different characteristics. Therefore Antroquinonol B and Antroquinonol C can be applied in inhibiting not only the growth of androgen-dependent prostate cancer cells LNCaP, but also androgen-independent prostate cancer cells DU-145. This is beneficial to the therapy of prostate cancer and recurrent prostate cancer.

In summary, Antroquinonol B and Antroquinonol C purified from extracts of *A. camphorata* can effectively inhibit the growth of breast cancer, lung cancer, hepatic cancer and prostate cancer. These compounds can be incorporated into medicinal compositions for treating the abovementioned cancer cells. The medicinal compositions include not only the compounds of Antroquinonol B and Antroquinonol C, but also the pharmaceutically accepted carries. The carriers include, but are not limited to, excipients such as water, fillers such as sucrose or starch, binders such as cellulose derivatives, diluents, disintegrants, absorption enhancers or sweeteners. The inventive composition can be manufactured through mixing the compounds of Antroquinonol B or Antroquinonol C with at least one of the carriers by means of conventional methods known in the pharmaceutically technical field, which can be formulated, but are not limited to, as a powder, tablet, capsule, pellets, granules or other liquid formulation.

What is claimed is:

1. A compound having the following formula, wherein X is hydroxyl (—OH) or methoxy (—$OCH_3$)

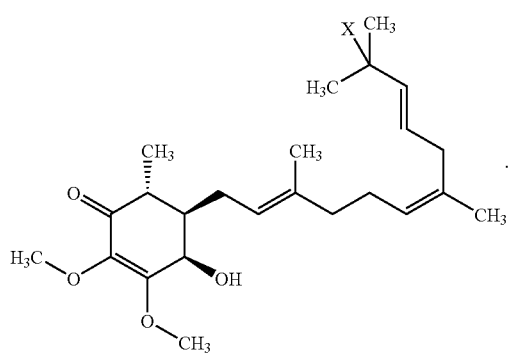

2. The compound as claimed in claim 1, wherein the compound is isolated from *Antrodia camphorata*.

3. The compound as claimed in claim 1, wherein the compound is Antroquinonol B when x is hydroxyl (OH).

4. The compound as claimed in claim 3, wherein the compound Antroquinonol B is isolated from *Antrodia camphorata*.

5. The compound as claimed in claim 1, wherein the compound is Antroquinonol C when x is methoxy ($OCH_3$).

6. The compound as claimed in claim 5, wherein the compound Antroquinonol C is isolated from *Antrodia camphorata*.

7. A compound as claimed in claim 3 used in inhibiting growth of cancer cells, wherein the cancer cells are breast cancer cells, hepatic cancer cells, or prostate cancer cells.

8. The compound as claimed in claim 7, wherein the breast cancer cells are selected from the group consisting of: breast cancer cell line MCF-7; and breast cancer cell line MDA-MB-231.

9. The compound as claimed in claim 7, wherein the hepatic cancer cells are selected from the group consisting of: hepatic cancer cell line Hep3B; and hepatic cancer cell line HepG2.

10. The compound as claimed in claim 7, wherein the prostate cancer cells are selected from the group consisting of: prostate cancer cell line LNCaP; and
prostate cancer cell line DU145.

11. A medicinal composition used in inhibiting growth of tumor cells, which comprises a compound as claimed in claim 3 and a pharmaceutically-acceptable carrier, wherein the tumor cells are selected from the group consisting of: breast cancer, hepatic cancer, and prostate cancer.

12. A compound as claimed in claim 5 used in inhibiting growth of cancer cells, wherein the cancer cells are breast cancer cells, hepatic cancer cells, or prostate cancer cells.

13. The compound as claimed in claim 12, wherein the breast cancer cells are selected from the group consisting of: breast cancer cell line MCF-7; and breast cancer cell line MDA-MB-231.

14. The compound as claimed in claim 12, wherein the hepatic cancer cells are selected from the group consisting of: hepatic cancer cell line Hep3B; and hepatic cancer cell line HepG2.

15. The compound as claimed in claim 12, wherein the prostate cancer cells are selected from the group consisting of: prostate cancer cell line LNCaP; and prostate cancer cell line DU145.

16. A medicinal composition used in inhibiting growth of tumor cells, which comprises a compound as claimed in claim 5 and a pharmaceutically-acceptable carrier, wherein the tumor cells are selected from the group consisting of breast cancer, hepatic cancer, and prostate cancer.

* * * * *